United States Patent [19]

Kan et al.

[11] Patent Number: 4,465,638

[45] Date of Patent: Aug. 14, 1984

[54] PROCESS FOR USING SEDIMENTS DEVELOPED DURING STORAGE OF PURE MDI

[75] Inventors: Peter T. Kan, Plymouth; Robert L. Schaaf, Wyandotte, both of Mich.; Lewis N. Medaugh, Kinnelon, N.J.; William E. Volz, Baton Rouge, La.

[73] Assignee: BASF Wyandotte Corporation, Wyandotte, Mich.

[21] Appl. No.: 459,463

[22] Filed: Jan. 20, 1983

[51] Int. Cl.$^3$ .................................. C07C 119/048
[52] U.S. Cl. ..................... 260/453 SP; 260/453 AM
[58] Field of Search ................. 260/453 SP, 453 AM

[56] References Cited

U.S. PATENT DOCUMENTS

| | | | |
|---|---|---|---|
| 3,274,225 | 9/1966 | Saunders et al. | 260/453 SP |
| 3,366,661 | 1/1968 | Anderson | 260/453 SP |
| 3,694,323 | 9/1972 | Cooper et al. | 260/453 SP X |

Primary Examiner—Dolph H. Torrence
Attorney, Agent, or Firm—Norbert M. Lisicki

[57] ABSTRACT

This invention relates to a process for utilizing the sediments in pure MDI which comprises
(a) heating the sediments at temperatures of 180° C. to 250° C. for 0.25 hour to 6 hours in the presence of crude MDI; and
(b) cooling the product to a temperature of 60° C. or less within 5 minutes.

The sediment-free crude MDI which results can then be used for the preparation of polyurethane products.

5 Claims, No Drawings

PROCESS FOR USING SEDIMENTS DEVELOPED DURING STORAGE OF PURE MDI

BACKGROUND OF THE INVENTION

1. Field of the Invention

This invention relates to a process for utilizing the sediment which forms in pure MDI during storage. The process involves heating the sediment to a temperature of 180° C. to 250° C. for 0.25 hour to 6 hours in the presence of crude MDI.

2. Description of the Prior Art

Commercially available pure MDI is a mixture containing abut 99 percent by weight of 4,4'-methylenediphenyldiisocyanate and about 1 percent by weight of 2,4'-methylenediphenyldiisocyanate. It is a solid at ambient temperatures and has a melting point of 37° C. It also has a tendency to form sediments. Evidence indicates that the sediment which forms when pure MDI is stored at 40° C. to 60° C. is a mixture of MDI dimer and polyuretdiones of varied composition:

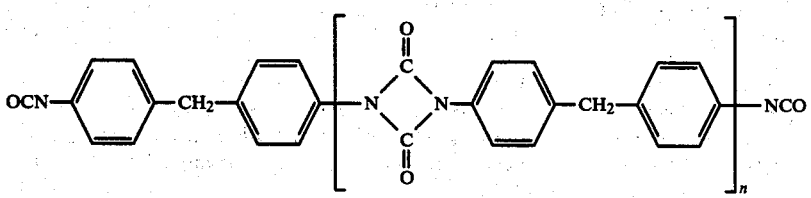

where n=1 for MDI dimer and n=2 or more for polyuretdiones. This conclusion is based on comparison of the precipitate with purified MDI dimer, as regards solubility, isocyanate content, melting point, and infrared analysis of isolated components.

On the other hand, similar data suggest that the sediments found in crude MDI, such as those described in U.S. Pat. Nos. 3,274,225 and 3,366,661, are a mixture of monouretdiones and do not contain polyuretdiones.

The rate of sediment formation in pure MDI is greatly influenced by temperature. It is well known that pure MDI must be stored at −20° C. to 0° C., or at 43° C. (as a liquid) to minimize sediment formation.

Storage at 0° C. is both costly and inconvenient and requires melting before use. When stored at 43° C., pure MDI still develops sediments at the rate of about 0.05 to 0.1 weight percent per week. The amount of sediment will exceed its limit of solubility in pure MDI after about 1.5 months to 2 months. Therefore, the material stored must be used quickly or filtered to remove the sediments. The filtered sediment not only represents a yield loss, but also is expensive in its disposal. Therefore, there is a need to develop methods which utilize the sediments which form in pure MDI.

SUMMARY OF THE INVENTION

This invention relates to a process for utilizing the sediments in pure MDI which comprises
 (a) heating the sediments at temperatures of 200° C. to 230° C. for about 0.5 hour to about 2 hours in the presence of crude MDI; and
 (b) cooling the product to a temperature of 60° C. or less within 5 minutes.

The crude MDI which results is essentially sediment free, is enriched with MDI, and can then be used for the preparation of polyurethane products.

DESCRIPTION OF THE PREFERRED EMBODIMENTS

For purposes of describing and claiming this invention, pure MDI is defined as 4,4'-methylenediphenyldiisocyanate or mixtures of 4,4'-methylenediphenyldiisocyanate and 2,4'-methylenediphenyldiisocyanate such that the 4,4'-isomer constitutes at least 95 percent by weight of the mixture. Crude MDI is defined as a mixture of methylenediphenyldiisocyanates and polymethylene polyphenylene polyisocyanates such that the average functionality is from 2.2 to 3.0.

In order to practice this invention, sediments from pure MDI are recovered by separation techniques well known in the art, such as decantation of the liquid MDI, and filtration.

The recovered sediment is mixed with crude MDI and heated to a temperature of 180° C. to 250° C. preferably from 200° C. to 230° C. The heating is continued from 0.25 hour to 6 hours, preferably from 0.5 hour to 2 hours. Then it is cooled to 60° C. or less within 5 minutes. The weight ratio of the sediment to the crude MDI is from 1 to 20, preferably from 5 to 10.

The examples which follow will illustrate in greater detail the practice of this invention and illustrate the best mode for carrying out this invention. The parts referred to are by weight and the temperatures are in degrees centigrade unless otherwise specified.

EXAMPLES 1-9

Eighteen parts of crude MDI were stirred and heated into a flask equipped with a stirrer, thermometer, nitrogen inlet, heating mantle, and a Vigreux column topped with a drying tube. At 230° C. under a slow nitrogen stream, 2 parts of sediments from pure MDI were added, and the mixture was stirred at 230° C. for 30 minutes. The mixture was immediately cooled to 60° C. with an ice bath. It was then filtered with suction and the filtrate analyzed for uretdione content by infrared. The solid was separately washed thoroughly with toluene and dried. When the concentration of precipitate employed was 1 percent instead of 10 percent, the amount of crude MDI was increased five-fold to provide greater accuracy in the weighing of insoluble material. With pure MDI in place of crude MDI, the hot mixture was poured into toluene and the filtered solution stripped prior to uretdione analysis.

The specific reaction conditions and results are summarized in Table I which follows.

TABLE I

| Example | Crude MDI | Uretdione[b] | Sediment Added % by weight | Temp. °C. | Time, Hours | Insolubles (at reaction temperature) % by weight | Soluble Uretdione (at room temperature) % by weight |
|---|---|---|---|---|---|---|---|
| 1 | Crude MDI-S[a] | A | 10 | 230 | 0.5 | 0.018 | 0.60 |
| 2 | " | A | " | " | 0.25 | 0.26 | 0.56 |
| 3 | " | A | " | 215 | 0.5 | 2.2 | 0.84 |
| 4 | " | A | " | " | 1.0 | 1.4 | 0.58 |
| 5 | " | A | 1.0 | 220 | " | 0.05 | 0.78 |
| 6 | " | A | " | 200 | " | 0.24 | 0.94 |
| 7 | Crude MDI-M[a] | A | 10 | 200 | 3.0 | 6.6 | 0.86 |
| 8 | " | B | " | " | 6.0 | 4.0 | 0.84 |
| 9 | " | C | " | " | 3.0 | 1.0 | 0.86 |
| Comparison | Pure MDI[c] | A | " | 230 | 0.5 | 0.0044 | 6.3[d] |

[a]Crude MDI-S contained 1.14 percent soluble uretdione and 440 ppm acidity. Crude MDI-M contained 0.94 percent soluble uretdione and 780 ppm acidity.
[b]Uretdione A was isolated from pure MDI and gave only 13 percent MDI uretdione upon extraction with boiling toluene and cooling the extract. Uretdione B was the insoluble solid isolated from run 7 (the 6.6 percent). Uretdione C was isolated from pure MDI and not further characterized.
[c]Pure MDI contains approximately 99.5 percent by weight of 4,4'-methylenediphenyldiisocyanate, and 0.5 percent by weight of 2,4-methylenediphenyldiisocyanate.
[d]Measurements were made at approximately 43° C. since pure MDI is a solid at room temperature.

These examples illustrate the effectiveness of the described process in causing the uretdiones from pure MDI to disassociate to form MDI. The examples show that the optimum condition for dissociating the uretdiones is a temperature of about 230° C. over a time period of one-half hour to one hour. The table indicates that most of the uretdione which was solubilized dissociated into MDI. On the other hand, the Comparison Example shows that this process is not effective if pure MDI is used instead of crude MDI. The uretdione is solubilized in pure MDI but does not disassociate to form MDI. Moreover, upon standing, the uretdione will eventually precipitate since the 6.3 percent uretdione level far exceeds its solubility limit in pure MDI at 0.5 percent.

The embodiments of the invention in which an exclusive privilege or property is claimed are defined as follows:

1. A process for utilizing the sediments of pure MDI which comprises
   (a) heating the sediments at temperatures of about 180° C. to about 250° C. for about 0.25 hour to about 6 hours in the presence of crude MDI; and
   (b) cooling the product to a temperature of about 60° C. or less within about 5 minutes.

2. The process of claim 1 wherein the product is cooled to a temperature of 60° C. within about 5 minutes.

3. The process of claim 2 wherein the weight ratio of sediment to crude MDI is from about 1 to about 20.

4. The process of claim 3 wherein the heating in step (a) takes place at temperatures of about 200° C. to about 230° C.

5. The process of claim 4 wherein the heating takes place over a period of about 0.5 to about 2 hours.

* * * * *